US00PP23402P2

(12) United States Plant Patent
Petit

(10) Patent No.: US PP23,402 P2
(45) Date of Patent: Feb. 19, 2013

(54) ***HEMEROCALLIS* PLANT NAMED 'SPD 06-08'**

(50) Latin Name: ***Hemerocallis* hybrid**
Varietal Denomination: SPd 06-08

(76) Inventor: Ted L. Petit, McIntosh, FL (US)

( * ) Notice: Subject to any disclaimer, the term of this patent is extended or adjusted under 35 U.S.C. 154(b) by 111 days.

(21) Appl. No.: 13/134,126

(22) Filed: May 31, 2011

(51) Int. Cl.
*A01H 5/00* (2006.01)

(52) U.S. Cl. ..... Plt./312

(58) Field of Classification Search ..... Plt./312
See application file for complete search history.

*Primary Examiner* — June Hwu
(74) *Attorney, Agent, or Firm* — Penny J Aguirre

(57) ABSTRACT

A new cultivar of *Hemerocallis* named 'SPd 06-08', characterized by its flowers that are peach to melon with highlights of tangerine and pink in color, its flowers that fully open under cool growing conditions and are self cleaning, its flower petals that are orbicular in shape and heavy in substance with ruffled edges, its blooming habit that commences very early in the season with continuous re-bloom until frost on recurrent, branched scapes with high bud counts, its foliage that is evergreen, semi-evergreen or dormant depending on the growing climate with suitability in a variety of growing climates, its compact plant habit with grass-like foliage, its fast multiplication rate, and its hardiness at least in U.S.D.A. Zones 4 to 11, and its high tolerance to daylily rust.

2 Drawing Sheets

Botanical classification: *Hemerocallis* hybrid.
Cultivar designation: 'SPd 06-08'.

CROSS REFERENCE TO A RELATED APPLICATION

This application is co-pending with U.S. Plant Patent Application and Patents filed for plants derived from the same breeding program that are entitled *Hemerocallis* Plant Named 'Spd 06-02' (U.S. Plant Pat. No. 22,181), *Hemerocallis* Plant Named 'Spd 06-01' (U.S. Plant Pat. No. 23,096), *Hemerocallis* Plant Named 'Spd 06-11' (U.S. Plant Pat. No. 23,095), *Hemerocallis* Plant Named 'Spd 06-12' (U.S. Plant patent application Ser. No. 13/134,127), *Hemerocallis* Plant Named 'Spd 06-13' (U.S. Plant Pat. No. 23,112), and *Hemerocallis* Plant Named 'Spd 06-16' (U.S. Plant Pat. No. 23,113).

BACKGROUND OF THE INVENTION

The present invention relates to a new and distinct cultivar of *Hemerocallis* plant of hybrid origin, botanically known as *Hemerocallis* 'SPd 06-08' and will be referred to hereafter by its cultivar name, 'SPd 06-08'.

The new cultivar was developed through an on-going breeding program conducted by the Inventor in McIntosh, Fla. The objectives of the breeding program are to develop new cultivars of tetraploid *Hemerocallis* that exhibit early and continuous flowering on recurrent, branched scapes with high bud counts and flowers that fully open during cool conditions, have bright flower color, heavy petal substance, and clean shedding of the old flowers to allow new buds to fully develop. Further objectives of the breeding program include developing plants that exhibit a high multiplication rate, short blooms stalks, foliage that is grass-like and compact, cold and heat hardiness and resistance to daylily rust.

The Inventor made crosses in summer of 2005 between specific unnamed proprietary male and female parents in his breeding line and pooled all the resulting seed from his crosses and evaluated the resulting seedlings based on the objectives of the breeding program. 'SPd 06-08' was selected as a single unique plant from the resulting seedlings in summer of 2006. The specific parents are unknown.

Asexual reproduction of the new cultivar was first accomplished by division in McIntosh, Fla. in 2006 by the Inventor. Propagation by division and tissue culture has determined that the characteristics of this cultivar are stable and are reproduced true to type in successive generations.

SUMMARY OF THE INVENTION

The following traits have been repeatedly observed and represent the characteristics of 'SPd 06-08'. These attributes in combination distinguish 'SPd 06-08' as a new and distinct cultivar of *Hemerocallis*.

1. 'SPd 06-08' exhibits flowers that are about 10 cm in diameter and are peach to melon with highlights of tangerine and pink in color.
2. 'SPd 06-08' exhibits flower petals that are orbicular in shape and heavy in substance with have ruffled edges.
3. 'SPd 06-08' exhibits a blooming habit that commences very early in the season with continuous rebloom until frost on recurrent, branched scapes with high bud counts.
4. 'SPd 06-08' exhibits flowers that fully open under cool growing conditions and cleanly shed spent flowers to allow new buds to fully develop.
5. 'SPd 06-08' has foliage that is evergreen, semi-evergreen or dormant depending on the growing climate, which allows its suitability to a variety of growing climates.
6. 'SPd 06-08' is a tetraploid.
7. 'SPd 06-08' exhibits a compact plant habit with grass-like foliage with short blooms scapes that allow for ease of transporting of finished plants.
8. 'SPd 06-08' is readily propagated by division or tissue culture and exhibits a fast multiplication rate (fan increase).
9. 'SPd 06-08' is cold and heat hardy at least in U.S.D.A. Zones 4 to 11.
10. 'SPd 06-08' exhibits a very high tolerance to daylily rust (*Puccinia hemerocallidis*).

The new cultivar can be most closely compared to the cultivars 'Mini Pearl' (not patented) and 'Sombrero Way' (not patented). Both cultivars are similar to 'SPd 06-08' in flower coloration. 'Mini Pearl' differs from 'SPd 06-08' in having taller flower scapes, in having less flowers that are smaller in size and do not open fully in cold weather, in blooming later in the season with less recurrent blooming, and in having a slower multiplication rate. 'Sombrero Way' differs from 'SPd 06-08' in having taller flower scapes, in having wider foliage that is less tolerant to rust, in having less flowers that do not open fully in cold weather, in commencing bloom later in the season with less recurrent blooming, and in having a much slower multiplication rate. 'SPd 06-08' can also be most closely compared to cultivars from the same breeding program. These cultivars differ from 'Spd 06-08' primarily in flower coloration. 'SPd 06-02' exhibits flowers that are golden yellow in color with maroon to burgundy red eyezones, 'SPd 06-01' exhibits flowers that are coral pink in color with rosy-red eyezones, 'SPd 06-11' exhibits flowers that are tomato red in color with a yellow-green throat, 'SPd 06-12' exhibits flowers that are burgundy rose in color with a darker burgundy eye, 'SPd 06-13' exhibits flowers that are light yellow in color, 'SPd 06-16' exhibits flowers that are golden yellow in color with a gold-green throat.

BRIEF DESCRIPTION OF THE DRAWING

The accompanying colored photograph illustrates the overall appearance and distinct characteristics of the new *Hemerocallis*. The photographs were taken in early spring of a two year-old plant of 'SPd 06-08' as grown outdoors in a field plot from a single fan in McIntosh, Fla. without fungicide treatment, growth regulators or deadheading.

The photograph in FIG. 1 illustrates its early flowering, grass-like foliage, high bud counts, short scapes, and self-cleaning of blooms of 'SPd 06-08'.

Figure 1:
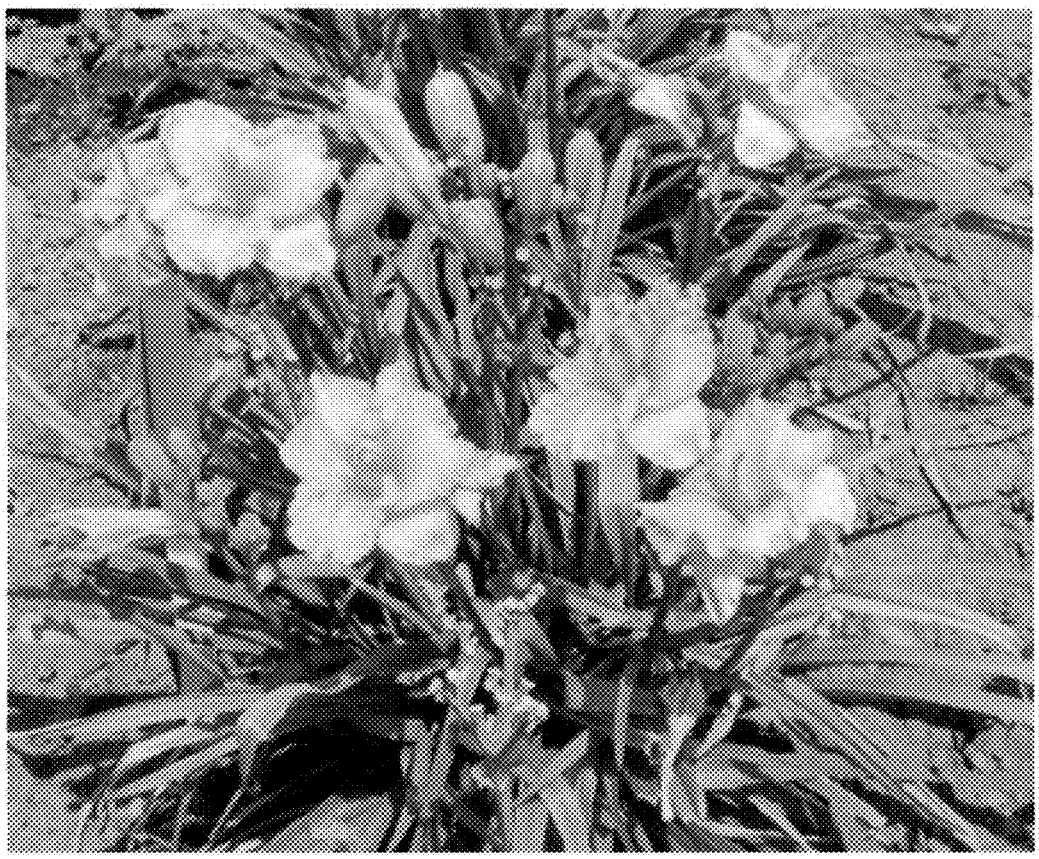
Figure 2:
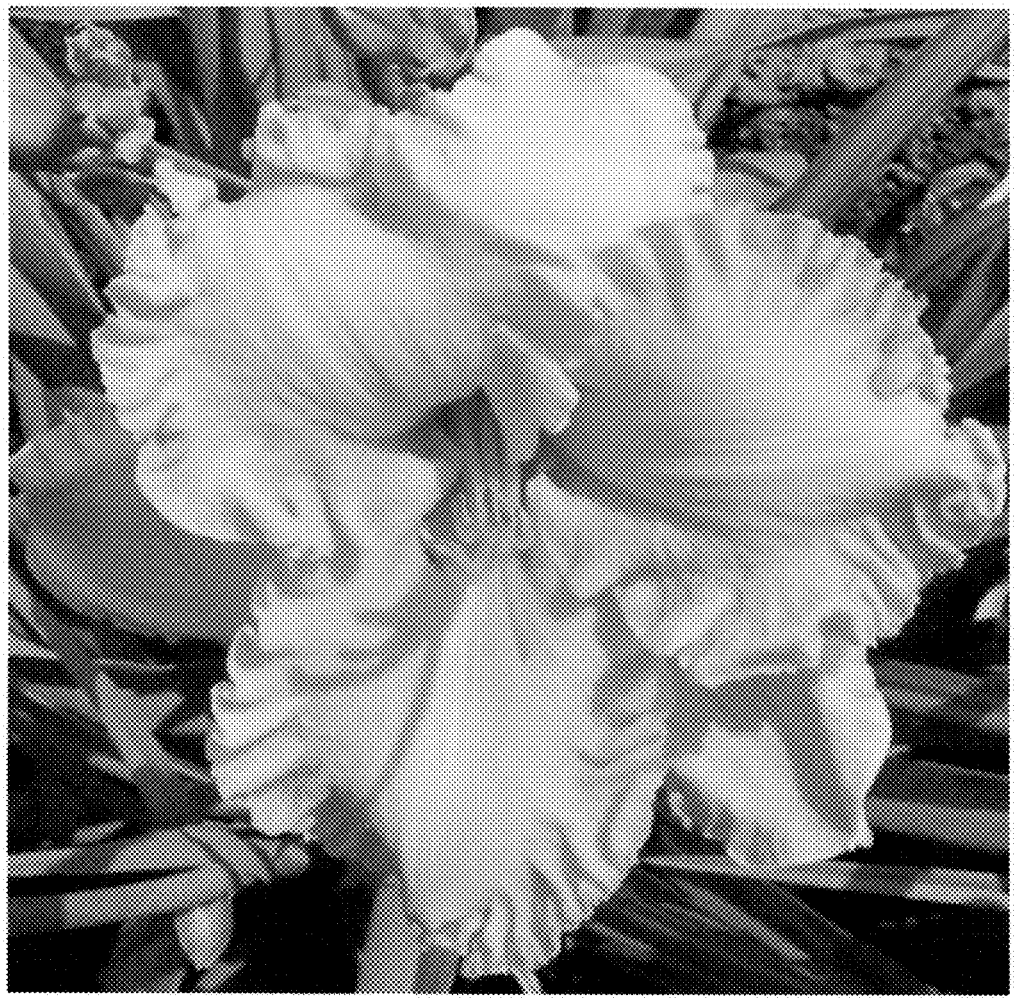

The photograph in FIG. 2 provides a close-up view of a flower of 'SPd 06-08'. The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of a 2 year-old plant of the new cultivar as grown outdoors in a 1-gallon container in McIntosh, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Commencing in March and recurrent until frost in Florida.

*Plant habit*.—Herbaceous perennial, compact grass-like foliage.

*Height and spread*.—Reaches about 35 cm in height and 30 cm in spread, flower scapes up to 35 cm in height.

*Hardiness*.—At least in U.S.D.A. Zones 4 to 11.

*Diseases and pests*.—Has been observed to be highly tolerant to daylily rust (*Puccinia hemerocallidis*).

*Root description*.—Fibrous roots.

*Propagation*.—Division and tissue culture.

*Growth rate*.—Vigorous with a high multiplication rate (5 fans per fan per season).

Foliage description:

*Leaf shape*.—Linear, grass-like.

*Leaf division*.—Simple.

*Leaf base*.—Sheathed to crown.

*Leaf apex*.—Narrowly acute.

*Leaf venation*.—Longitudinal, parallel, not prominent, same color as leaves.

*Leaf margins*.—Entire.

*Leaf attachment*.—Sheathed, not petiolate.

*Leaf arrangement*.—Equitant, fan-shaped.

*Leaf orientation*.—Held upright and slightly pendulant from mid section towards apex once matured.

*Leaf surface*.—Glabrous.

*Leaf color*.—Young leaves (upper and lower surface); a blend of 137C and 144A, mature leaves (upper and lower surface); a blend of 137A and 137C.

*Leaf size*.—Up to 47 cm in length, an average of 2 cm in width.

*Leaf quantity*.—About 47 leaves per one-gallon container.

Flower scape description:

*Scape shape*.—Oval, pithy.

*Scape number*.—1 to 2 per fan at one time, continuously produced until frost.

*Scape aspect*.—Straight, held upright.

*Scape size*.—Up to 35 cm in length and 9 mm in width, with branch portion an average of 12 cm in length and 7 mm in width.

*Scape color*.—A blend of 137A and 137C.

*Scape surface*.—Glabrous, slight sheen.

*Scape branching*.—Typically 2 branches per scape, internode length about 5 mm .

*Scape leaves*.—1 to 3 per branched scape fan, a blend of 137B and 144A in color, turning to a blend of 144A and 137C and then becoming papery with age, 1.5 cm to 11 cm in length, 1.2 cm to 1.5 cm in width, lanceolate to ovate in shape, sheathed base, acuminate apex, glabrous surface.

Flower description:

*Inflorescence type*.—Scape bearing an average of 10 single flowers per branched scape, one flower is open at a time.

*Inflorescence size*.—Varies with opening of flowers, an average of 12 cm in width and 10 cm in depth on per branch.

*Lastingness of flowers*.—About 24 hours, self cleaning.

*Flower size*.—An average of 85 cm in depth and 10.5 cm in diameter.

*Flower fragrance*.—None.

*Flower number*.—16 to 20 per branched stem.

*Flower aspect*.—Upright to slightly outward.

*Flower bud*.—Oblong in shape, an average of 6.5 cm in length and 2.2 cm in width, color; blend of 9A and 144C, a blend of 150C and 144B at base, 144B at very tip, seams (visible petal portion) 18A.

*Flower attachment*.—Petiolate.

*Petal number*.—3.

*Petal shape*.—Orbicular and narrowing at base.

*Petal color*.—Upper surface; a blend of 21A and 20A with a mid rib of 26C with blush of 38C, throat (not distinct); blending of 14B with slight blush of 144C, lower surface; a blend of 26B and 26C.

*Petal surface*.—Glabrous and lustrous on upper surface, glabrous and satiny on lower surface.
*Petal margins*.—Ruffled, ruffled and wavy.
*Petal apex*.—Obtuse.
*Petal base*.—Cuneate to truncate at very base.
*Petal size*.—Average of 6.2 cm in length to tube and 4.5 cm in width.
*Petal aspect*.—Slightly recurved.
*Sepal number*.—3.
*Sepal shape*.—Elliptic-broadly lanceolate.
*Sepal margin*.—Entire, slightly wavy, edges slightly curved under.
*Sepal size*.—Average of 6.2 cm in length, 3.4 cm in width.
*Sepal aspect*.—Moderately recurved.
*Sepal surface*.—Glabrous and lustrous on upper surface, glabrous and satiny on lower surface.
*Sepal apex*.—Broadly acute with mucronate tip on lower surface.
*Sepal base*.—Fused, cuneate to tube portion.
*Sepal color*.—Upper surface; a blend of 26B and 26C, lower surface; 26C on edges and center portion a blend of 18A and 26C that blends with 151D near base, mucronate tip 144B.
*Tube portion*.—A blend of a blend of 150C and 144B, 1.6 cm in length and 1 cm in width, satiny surface.
*Peduncles*.—An average of 3 cm in length and 3 mm in width, oval in shape, strong, color a blend of 137A and 137C, held at about 45° relative to stem.
*Pedicels*.—An average of 5 mm in length and 3 mm in width, oval in shape, strong and stout, color, a blend of 137A and 137C.

Reproductive organs:
*Gynoecium*.—Pistil; 1, style; 8 cm in length, style; 4.9 cm in length, 2 mm in width color 11B at base blend towards apex with 26C and 31C, stigmas; minute, 11D in color, ovary; oblong in shape, 0.8 cm in length and 4.5 mm in width, 145A in color.
*Androecium*.—Stamens; 6, anthers; 6 mm in length and 2 mm in width, 200A in color; filaments; 4.5 cm in length, 1 mm in width, color a blend of 26C and 31C, pollen; abundant and 22A in color.
*Fruit/seeds*.—None observed.

It is claimed:

1. A new and distinct cultivar of *Hemerocallis* plant named 'SPd 06-08' as herein illustrated and described.

* * * * *